(12) United States Patent
Singh et al.

(10) Patent No.: US 8,778,689 B1
(45) Date of Patent: Jul. 15, 2014

(54) SYNTHESIS AND USE OF CHIRAL IONIC LIQUIDS

(75) Inventors: Gurdial Singh, St. Augustine (TT);
Patrice G. J. Plaza, Arima (TT);
Bhoomendra A. Bhongade, St. Augustine (TT)

(73) Assignee: The University of the West Indies, Trinidad, West Indies ( * ) Notice: Subject to any disclaimer, the term of this patent is extended or adjusted under 35 U.S.C. 154(b) by 488 days.

(21) Appl. No.: 12/126,639

(22) Filed: May 23, 2008

Related U.S. Application Data

(60) Provisional application No. 60/924,630, filed on May 23, 2007.

(51) Int. Cl.
| | | |
|---|---|---|
| *C07H 19/052* | (2006.01) | |
| *C07H 1/06* | (2006.01) | |
| *G01N 21/31* | (2006.01) | |
| *G01N 21/33* | (2006.01) | |
| *G01N 21/35* | (2014.01) | |
| *G01N 24/08* | (2006.01) | |

(52) U.S. Cl.
USPC ............ 436/98; 436/172; 436/173; 536/28.8; 536/127

(58) Field of Classification Search
CPC ........ C07H 19/052; C07H 1/06; G01N 21/31; G01N 21/33; G01N 21/35; G01N 24/087
USPC .................... 436/98, 172, 173; 536/28.8, 127
See application file for complete search history.

(56) References Cited

U.S. PATENT DOCUMENTS

| 6,900,313 B2 | 5/2005 | Wasserscheid et al. |
|---|---|---|
| 7,256,152 B2 | 8/2007 | Olivier-Bourbigou et al. |
| 2010/0041869 A1* | 2/2010 | Chan et al. .................... 530/333 |

OTHER PUBLICATIONS

Reist, E. et al., Journal of Organic Chemistry, "Potential Anticancer Agents. LXXVI. Synthesis of Purine Nucleosides of B-D-Arabinofuranose", vol. 27, pp. 3274-3279, (Sep. 1962).*
Chan, T. H. et al., Synthesis, "Ionic-Tag-Assisted Oligosaccharide Synthesis", No. 10, pp. 1645-1651 (Jan. 2006).*
Brown, T. et al., J.C.S. Perkin I, "Purines, Pyrimidines, and Imidazoles. Part 51. New Syntheses of Some 5-Alkyl- and 5-Dialkyl-aminoimidazoles. 3-Alkylimidazolium Nucleosides and 3-Alkylpurines". p. 3107-3112, (1979).*
Baudequin et al. "Chiral ionic liquids, a renewal for the chemistry of chiral solvents? Design, synthesis and applications for chiral recognition and asymmetric synthesis" Tetrahedron: Asymmetry 16:3921-3945 (2005).
Ding & Armstrong "Chiral ionic liquids: Synthesis and applications" Chirality 17:281-292 (2005).
Murugesan & Linhardt "Ionic liquids in carbohydrate chemistry—Current trends and future directions" Curr. Org. Synth. 2:437-451 (2005).
Pandey "Analytical applications of room-temperature ionic liquids: A review of recent efforts" Anal. Chim. Acta 556:38-45 (2006).
Plaza et al. "Synthesis of chiral carbohydrate ionic liquids" Synlett 2008:2973-2976 (2008) and erratum at 2009:332 (2009).
Tran et al. "Chiral ionic liquid that functions as both solvent and chiral selector for the determination of enantiomeric compositions of pharmaceutical products" Anal. Chem. 78:1349-1356 (2006).
Welton "Room-temperature ionic liquids. Solvents for synthesis and catalysis" Chem. Rev. 99:2071-2083 (1999).

* cited by examiner

*Primary Examiner* — Shaojia Anna Jiang
*Assistant Examiner* — Bahar Craigo
(74) *Attorney, Agent, or Firm* — Nixon & Vanderhye PC

(57) ABSTRACT

We disclose the synthesis and use of chiral ionic liquids based on a substituted pentose, furanose, hexose, or pyranose sugar. The compounds and processes to make or use them are provided.

16 Claims, No Drawings

SYNTHESIS AND USE OF CHIRAL IONIC LIQUIDS

CROSS-REFERENCE TO RELATED APPLICATIONS

This application claims priority benefit of Application No. 60/924,630, filed May 23, 2007; which is incorporated by reference.

BACKGROUND OF THE INVENTION

This invention relates to the synthesis and use of chiral ionic liquids based on a substituted pentose, furanose, hexose, or pyranose sugar. The compounds and processes to make or use them are provided.

Ionic liquids have been the subject of much recent research. The surge in interest in ionic liquids has been due chiefly to their potential to replace volatile organic compounds as the solvent in laboratory and industrial applications (Pandey, *Anal. Chim. Acta*, 556:38-45, 2006). Hazardous chemicals are characterized by their volatility because they are easily evaporated from a reaction mixture or reactor, and then inhaled by workers. In contrast, ionic liquids do not evaporate under conditions typical for chemical reactions, separations, and analyses. Released into the environment, volatile organic compounds may also act directly as toxins or degrade into pollutants. In addition to their environmentally friendly nature, ionic liquids have been used in a variety of chemical applications including catalysis, chromatography, and spectrometry. As yet, the full scope of ionic liquids has not been investigated and much effort is being put into understanding the properties and behavior of this class of solvents (Welton, *Chem. Rev.*, 99:2071-2083, 1999).

The unique environment provided by ionic liquids is thought to be a solution to many reactions which are unfavorable in conventional solvents. Chiral ionic liquids have renewed interest in using chiral solvents to control stereoselectivity (Baudequin et al., *Tetrahedron: Asymmetry*, 16:3921-3945, 2005). Unlike conventional chiral solvents, chiral ionic liquids are synthesized easily in good yields. Chiral ionic liquids may be based on amino acid, hydroxyl acid, amine, amino alcohol, terpene, and alkaloid compounds or they may be made by asymmetric synthesis. They may possess central, axial, or planar chirality; their chirality may arise from either the anion or cation of the salt. Here, we show that substituted sugars possessing a number of different chiral centers may be used to synthesize chiral ionic liquids.

Therefore, it is an objective of the invention to provide a novel class of chiral ionic liquids for use as solvents in chemical reactions, separations, and analyses. A long-felt need is addressed thereby. Further objectives and advantages of the invention are described below.

SUMMARY OF THE INVENTION

The invention is a novel class of compounds used as chiral ionic liquids. It is also directed to (a) their synthesis and isolation and (b) their use as the solvent in chemical reactions, separations, and analyses. This class of compounds is based on a monosaccharide with five or six atoms (usually carbon, but optionally one may be an oxygen) in the sugar ring; the sugar may occur naturally or be artificial. But they are manufactured and do not occur naturally. The compound may be used as a solvent at least to partially or substantially solubilize one or more chemicals. In preferred embodiments, a sugar may be modified by replacing one or more hydroxyl groups with protecting groups.

The chiral ionic liquid comprises an anion and a cation. A sugar may form the cation by replacing all but one hydroxyl groups with protecting groups and replacing the one hydroxyl group with an imidazolium group forms the cation. The sugar may be a pentose, furanose, hexose, or pyranose. It may be in either D- or L-form; it may be in either alpha or beta configuration. The anion may be halide, acetate, aluminate, amide, borate, chlorate, cyanide, imidazole, imide, imino, iodate, nitrate, nitrite, phosphate, phosphonate, sulfate, or sulfonate.

It is another object of the invention to use the chiral ionic liquid in a chemical reaction. The reaction may be used for an asymmetric synthesis, crystallization of solute, diastereoselective synthesis, enantioselective synthesis, folding a denatured protein, stereoselective synthesis, etc.

A further object of the invention is to use the chiral ionic liquid in a chemical separation. Separation may be performed on one or more chemicals, or a mixture thereof. Chromatography is preferred, but any separation technique may be used; alternatively, it may be used in an extraction to partition an eluate between liquid phases. The eluate may be at least partially or substantially solubilized in the chiral ionic liquid, or may be removed therefrom by its relative insolubility.

Another object of the invention is to use the chiral ionic liquid in a chemical analysis. Analysis may be performed on a purified chemical or a mixture of chemicals that have been at least partially or substantially solubilized in the chiral ionic liquid. Spectroscopy is preferred, but any analytical technique may be performed on an analyte with the chiral ionic liquid used as solvent.

Yet another object of the invention is to make the chiral ionic liquid. All but one hydroxyl functional group of the sugar may be blocked by one or more different protecting groups, and the one hydroxyl functional group may be replaced with N-methylimidazolium to form a cation. At least one protecting group is benzyl. The anion may be easily replaced. The compound produced thereby may be subjected to further processing (e.g., isolation from unreacted reagents and/or undesired by-products). It should be noted, however, that a claim directed to a product of the invention is not necessarily limited to these processes unless the particular steps of the process are recited in the product claim.

Further aspects of the invention will be apparent to the skilled artisan from the following description of specific embodiments and the claims, and generalizations thereto.

DESCRIPTION OF SPECIFIC EMBODIMENTS OF THE INVENTION

A chiral ionic liquid of the invention is comprised of a cation which is based on a sugar and an anion. The sugar may be a monosaccharide with a five atom ring (e.g., pentose or furanose) or a six atom ring (e.g., hexose or pyranose). A pentose may have an aldehyde functional group at position 1 (aldopentose) or a ketone functional group at position 2 (ketopentose). Likewise, a hexose may have an aldehyde functional group at position 1 (aldohexose) or a ketone functional group at position 2 (ketohexose). The aldehyde and ketone functional groups can react with neighboring hydroxyl functional groups to form intramolecular hemiacetals or hemiketals, respectively. Furanose and pyranose are cyclic hemiacetals. In alpha configuration, the hydroxyl group attached to the anomeric carbon is below the plane of the ring; the hydroxyl group attached to the anomeric carbon is above the plane of the ring in beta configuration. While many of these sugars sugar occur naturally, others must be synthesized artificially. But a chiral ionic liquid of the invention is manufactured and does not occur naturally.

The sugars include those contain functional groups such as aldehydes (i.e., aldoses) or ketones (i.e., ketoses). An aldopentose has three chiral centers. There are eight possible stereoisomers of aldopentose: D- and L-forms of ribose, arabinose, xylose, and lyxose. An aldohexose has four chiral centers. There are 16 possible stereoisomers of aldohexose: D- and L-forms of allose, altrose, glucose, mannose, gulose, idose, galactose, and talose. A ketopentose has two chiral centers. There are four possible stereoisomers of ketopentose: D- and L-forms of ribulose and xylulose. A ketohexose has three chiral centers. There are eight possible stereoisomers of ketohexose: D- and L-forms of fructose, psicose, sobose, and tagatose.

Preferred sugars are α,β-D-arabinofuranose, α,β-L-arabinofuranose, α,β-D-ribofuranose, α,β-L-ribofuranose, α,β-D-xylofuranose, α,β-L-xylofuranose, α,β-D-galactofuranose, and α,β-L-galactofuranose. The starting sugar is a mixture of pyranose and furanose forms in solution, but it exists in the pyranose form as a solid. The sugar is made into a furanose structure in the first step of the reaction scheme shown below.

At atmospheric pressure, a compound of the invention may be liquid at a temperature from 20° C. to 250° C., preferably from 25° C. to 100° C. One or more chemicals dissolved in the liquid may be recovered by crystallization or distillation.

The anion may be a halide (e.g., fluoride, chloride, bromide, iodide), acetate, aluminate, amide, borate, chlorate, cyanide, imidazole, imide, imino, iodate, nitrate, nitrite, phosphate, phosphonate, sulfate, or sulfonate.

A chiral ionic liquid may be used as a solvent to partially or substantially solubilize one or more chemicals. They may be reactant(s) or product(s) or both of a chemical reaction. Thus, the chiral ionic liquid may be used as a solvent in the reaction. The reaction may be an asymmetric synthesis, crystallization of solute, diastereoselective synthesis, enantioselective synthesis, folding a denatured protein, stereoselective synthesis, etc.

A chiral ionic liquid may be used in a chemical separation. Chromatography is a preferred separation technique. The separation may be used for to separate one or more chemicals on the basis of their stereochemistry. A chiral ionic liquid may be the stationary phase or the mobile phase or both in chromatography. As the stationary phase, the chiral ionic liquid may be distributed on a solid support, it may be bonded to the solid support (bonded phase), or it may be immobilized on the solid support (immobilized phase). As the mobile phase, the chiral ionic liquid may at least partially or substantially solubilize the one or more chemicals. In a chiral or affinity separation, a chiral selector or affinity ligand may be in the stationary phase, and interaction of the one or more chemicals with the chiral selector or affinity ligand may increase retention time of the chemical(s) relative to the mobile phase. A competitor agent may be used to interfere or block this interaction. As an alternative, an extraction may use the chiral ionic liquid as a solvent immiscible with at least one other solvent. The eluate may be at least partially or substantially solubilized in the chiral ionic liquid (i.e., solvent phase) and partitioned into the other solvent (i.e., extraction phase), or vice versa.

A chiral ionic liquid may be used in a chemical analysis. Analysis may be performed on a purified chemical or a mixture of chemicals that have been at least partially or substantially solubilized in the chiral ionic liquid. Spectroscopy is a preferred analytical technique. The chemical(s) may interact with electromagnetic radiation (e.g., infrared, visible, or ultraviolet light) and these interactions may be plotted in a spectrogram. Absorption spectroscopy is analysis of a range of the electromagnetic radiation from a source absorbed by the chemical(s); emission spectroscopy is analysis of a range of the electromagnetic radiation emitted by the chemical(s) after absorption from the source. For example, nuclear magnetic resonance (NMR) spectroscopy analyzes the properties of nuclei in chemical(s) subjected to a magnetic field (i.e., their magnetic properties) and measures their absorption of radiofrequency radiation.

In general, but all one hydroxyl functional group of the sugar may be blocked by one or more protecting groups, and then the remaining hydroxyl functional group may be replaced with N-methylimidazolium or isopropyl N-methylimidazolium to form a cation. Protecting groups that may be used include acetate, methyl, benzoate, benzyl, substituted benenzyl (e.g., 4'-OMe, Cl), cyclic acetals, and silyl protecting groups (e.g., trimethylsilyl, tert-butyldimethylsilyl). See U.S. Pat. No. 6,693,178 for a list of other protecting groups that can be used when modifying the sugar. A benyzl ether protecting group is preferred but, depending on the particular sugar, other protecting groups such as 4,6-O-benzylidene (for pyranoses) or 2,3-O-isopropylidene may be used. More than one or all of the protecting groups may be the same. The primary benzyl protecting group may be selectively removed from the compound (e.g., hydrogenolysis at 5 to 30 atm of hydrogen in the presence of a palladium catalyst).

The reaction scheme illustrated below was employed to prepare a 2,3,5-tri-O-benzyl-D-arabinoside ionic liquid. Replacement of D-arabinose with its L-enantiomer was used to produce the corresponding L-enantiomeric ionic liquid. Similarly, benzyl-protected furanoses obtained from D-ribose, D-xylose, or D-galctofuranose were used to produce the corresponding ionic liquids. The chloride may be replaced with a variety of different anions.

The following examples further illustrate the invention, but do not necessarily restrict the claims thereto unless the relevant limitations are recited therein.

EXAMPLES

Example 1

2,3,5-tri-O-benzyl-1-N-methylimidazolium-β-D-arabinofuranosyl chloride 2,3,5-tri-O-benzyl-α,β-arabinofuranoside was prepared from commercially available D-arabinose in three steps according to Barker & Fletcher (*J. Org. Chem.*, 26:4605-4609, 1961).

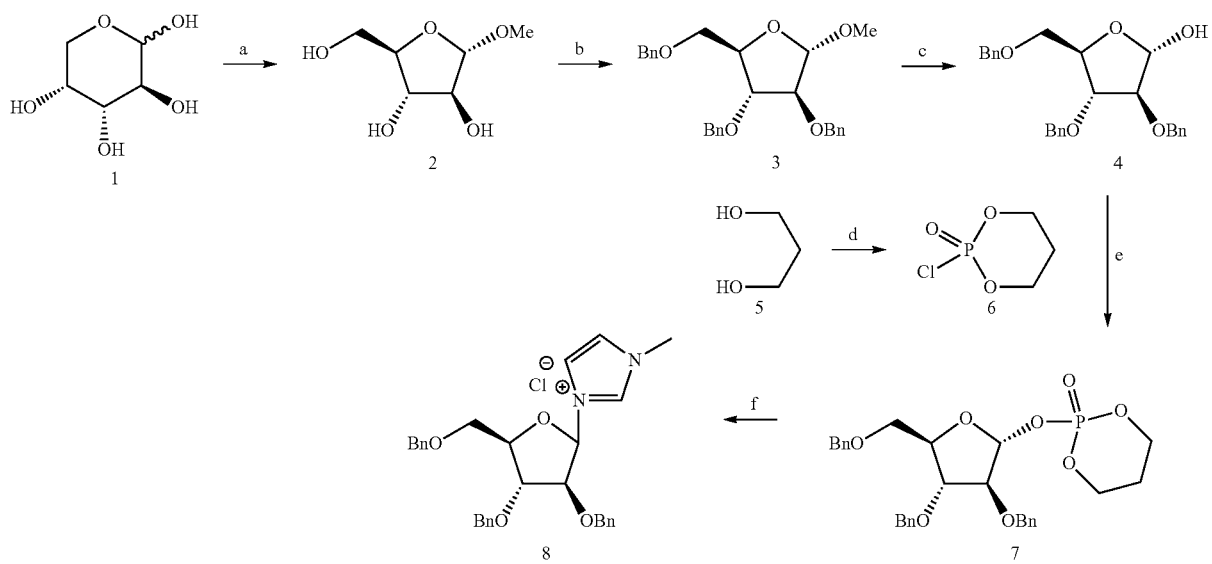

Scheme 1. Synthesis of 2,3,5-tri-O-benzyl-N—N-methylimidazole-β-arabinofuranosyl chloride. Reagents and Conditions: (a) Dry MeOH, p-TSA, 40° C., 20 h; (b) NaH, DMF, 0° C., 15 min, rt 15 min, Bu$_4$NI, BnBr, 4 h; (c) MeCN:H$_2$O: TFA (4:3:1), reflux 95° C., 12 h; (d) Dry CH$_2$Cl$_2$, POCl$_3$, NEt$_3$, 1 h 0° C. to rt; (e) Dry CH$_2$Cl$_2$, N-MeIm, 0° C. to rt, 16 h; (f) Dry CH$_2$Cl$_2$, TMSOTf, N-MeImHCl, −15° C. to rt.

2,3,5-tri-O-benzyl-α,β-D-arabinofuranoside (1.0 g, 2.4 mmol) was dissolved in dry dichloromethane (25 mL) and cooled to 0° C. under argon atmosphere. Propane-1,3-diylphosphorylchloride (0.78 g, 5.0 mmol) was added followed by 1-methylimidazole (0.5 mL, 6.3 mmol). The mixture was allowed to warm up to room temperature and stirred overnight (16 h). The reaction was then quenched with saturated NaHCO$_3$ (25 mL) and the organic layer washed with water (2×10 mL) and dried (Na$_2$SO$_4$). The solvent was then removed in vacuo to give 2,3,5-tri-O-benzyl-α,β-D-arabinofuranosyl-1-O-propane-1,3-diylphosphate (Li & Singh, *Tetrahedron Lett.* 42:6615, 2001). The crude sugar phosphate (N.B. 1-methylimidazole is still present) was re-dissolved in dry dichloromethane (25 mL) under argon atmosphere and cooled to −15° C. A catalytic amount of TMSOTf was added and the mixture stirred for 2 min. 1-methylimidazole hydrochloride (0.6 g, 5.0 mmol) was then added. The reaction mixture was allowed to warm up to room temperature and stirred until TLC (CHCl$_3$, MeOH; 80:20) showed the reaction had gone to completion (4 h). The mixture was then diluted with dichloromethane (25 mL) and washed with saturated aqueous NaHCO$_3$ (2×50 mL) and water (2×50 mL). The organic layer was dried (Na$_2$SO$_4$) and concentrated in vacuo to give a crude product, that was further purified by column chromatography (CHCl$_3$:MeOH, 80:20) to give the isolated compound (0.7 g, 58%). R$_f$ 0.26; $[\alpha]_D^{28}$=+55 (c1.1 CHCl$_3$); ν$_{max}$(film)/cm$^{-1}$ 3429, 3143, 3064, 3032, 2923, 2870, 1634, 1578, 1556, 1454, 1364, 1264, 1157, 1090, 1030, 748, 701, 638; $^1$H NMR (400 MHz) CDCl$_3$ δ$_H$(ppm): 3.60 3H/s, 3.62 1H/dd J=2.8, 10.9 Hz, 3.82 1H/dd J=3.0, 10.9 Hz, 4.13 1H/m, 4.23 1H/t J=6.78, 4.41 1H/d J=11.07 Hz, 4.48 1H/d J=11.05 Hz, 4.53 1H/d J=11.9 Hz, 4.64 2H/d J=6.3 Hz, 4.57 1H/m, 4.69 1H/d J=11.9 Hz, 6.46 1H/d J=5.8 Hz, 7.02 1H/m, 7.22-7.40 16H/m, 7.73 1H/m, 9.40 1H/s [Fluxional resonances: 3.72 3H/s, 6.91 1H/s, 7.08, 1H/s, 7.51 1H/s]; $^{13}$C NMR (100 MHz) CDCl$_3$ δ$_C$(ppm): 36.0, 68.0, 72.5, 73.5, 78.2, 81.0, 82.6, 87.3, 121.5, 122.5, 128.1, 127.9, 128.1, 128.2, 128.3, 128.5, 128.6, 135.5, 136.4, 137.1, 137.2; FABMS (m/z) 485.53.

Example 2

Procedure for Change of Anion from Chloride to Dicyanamide [dca]

In accordance with Forsyth et al. (*Chem. Comm.*, 714-715, 2002), AgNO$_3$ (13.67 g) was dissolved in water (40 mL) and treated with alkali Na$_2$CO$_3$ (4.27 g). The precipitated Ag$_2$CO$_3$ was filtered, washed, and dried to constant weight over H$_2$SO$_4$ and P$_2$O$_5$.

Na[dca] (3.56 g) in 2 M HCl (50 mL) was added to Ag$_2$CO$_3$ (11.03 g). The reaction proceeded with the evolution of CO$_2$ and H$_2$O to give Ag[dca] as a solid. The mixture was filtered and the product washed with water (100 mL).

Ag[dca] (1.9 g, 11 mmol) was added to a solution of the ionic liquid (5.73 g, 11 mmol) in 30 mL water and the resulting suspension stirred overnight. The mixture was then filtered and the solvent removed in vacuo to give the crude product which was redissolved in dichloromethane (30 mL), dried (Mg$_2$SO$_4$), and evaporated to give 2,3,5-tri-O-benzyl-1-N-methylimidazolium-β-D-arabinofuranosyl dicyanamide in 96% yield (5.82 g). $[\alpha]_D^{26}$=3.2 (c1.25 CHCl$_3$); $^1$H NMR (400 MHz) CDCl$_3$ δ$_H$(ppm): 3.55 (3H, s, N—CH$_3$), 3.59 (1H, dd, J=3.2, 10.9 Hz), 3.76 (1H, dd, J=3.2, 10.9 Hz) (H-5, H-5'), 4.09 (1H, m, H-4), 4.18 (1H, m, H-3), 4.38-4.65 (7H, H-2, benzylic-H), 6.22 (1H, d, J=5.5 Hz), 7.19-7.36 (16H, aromatic-H, imidazole-H), 7.73 (1H, bs, imidazole-H), 8.75 (1H, bs, imidazole-H); $^{13}$C (100 MHz) δ$_C$(ppm): 35.8 (—N—CH$_3$), 67.8 (C-5), 68.7, 68.8 (—N—C≡N) 72.2, 73.1 (benzylic-C), 77.9, 80.6, 82.3 (ring-C), 87.0 (C-1), 121.2, 122.5 (imidazole-C), 127.5-128.4 (aromatic-C), 135.4 (N—C≡N), 136.3, 136.9, 137.0 (sat. aromatic-C).

Example 3

2,3,5-tri-O-benzyl-1-N-methylimidazolium-β-L-arabinofuranosyl chloride

Synthesis and characterization of the compound was as in Example 1. $[\alpha]_D^{26}$=−12 (c1.0 CHCl$_3$); T$_d$=160° C.; $^1$H NMR (400 MHz) CDCl$_3$ δ$_H$(ppm): 3.56 (3H, s, N—CH$_3$), 3.59 (1H, dd, J=2.8, 10.9 Hz), 3.80 (1H, dd, J=3.03, 10.9 Hz) (H-5, H-5'), 4.16 (1H, m, H-4), 4.21 (1H, t, J=6.8 Hz, H-3), 4.39 (1H, d, J=11.0 Hz, benzylic-H), 4.46 (1H, d, J=11.0 Hz, benzylic-H), 4.48 (1H, d, J=12.1 Hz, benzylic-H), 4.54 (1H, t, J=6.2 Hz), 4.56-4.62 (2H, benzylic-H), 4.67 (1H, d, J=12.1 Hz, benzylic-H), 6.37 (1H, d, J=5.6 Hz), 7.06 (1H, bs, imidazole-H), 7.26-7.36 (15H, aromatic-H), 7.68 (1H, bs, imidazole-H), 9.20 (1H, bs, imidazole-H); $^{13}$C (100 MHz) δ$_C$(ppm): 36.1 (—N—CH$_3$), 68.0 (C-5), 72.6, 73.5 (benzylic-C), 78.1 (C-3), 80.9 (C-4), 82.6 (C-2), 87.3 (C-1), 121.6, 122.4 (imidazole-C), 127.7-128.5 (aromatic-C), 135.8 (N—C=N), 136.5, 137.2, 137.3 (sat. aromatic-C).

Example 4

Large-scale preparation of 2,3,5-tri-O-benzyl-1-N-methylimidazolium-β-D-arabinofuranosyl chloride 2,3,5-tri-O-benzyl-α,β-D-arabinofuranoside (10.0 g, 24 mmol) was dissolved in dry dichloromethane (250 mL), and then cooled to 0° C. under argon atmosphere. Propane-1,3-diyl-phosphoryl-chloride (7.5 g, 48 mmol) was added, followed by 1-methylimidazole (4.7 mL, 59 mmol). The mixture was allowed to warm up to room temperature and stirred overnight (16 h). The reaction was then cooled to −78° C. and TMSOTf (0.21 mL, 0.05 mmol) was added. The cooling bath was removed and the mixture stirred for 1 h. The mixture was then diluted with dichloromethane (25 mL), and washed with saturated aqueous NaHCO$_3$ (2×50 mL) and water (2×50 mL). The organic layer was dried (Na$_2$SO$_4$) and then concentrated in vacuo to give the crude product which was further purified via column chromatography (CHCl$_3$:MeOH, 95:5) to give the title compound (6.3 g, 51% yield). Column chromatography also resulted in the recovery of 2,3,5-tri-O-benzyl-α,β-D-arabinofuranoside (3.9 g). Thus, the overall yield of the reaction increases to 85%. [α]$_D^{26}$=+28 (c1.1 CHCl$_3$); ν$_{max}$(film)/cm$^{-1}$: 3429, 3143, 3064, 3032, 2923, 2870, 1634, 1578, 1556, 1454, 1364, 1264, 1157, 1090, 1030, 748, 701, 638; $^1$H NMR (400 MHz) CDCl$_3$ δ$_H$(ppm): 3.60 (3H, s, N—CH$_3$), 3.62 (1H, dd, J=2.8, 10.9 Hz), 3.82 (1H, dd, J=3.0, 10.9 Hz) (H-5, H-5'), 4.13 (1H, m, H-4), 4.23 (1H, t, J=6.8 Hz, H-3), 4.41 (1H, d, J=11.1 Hz, benzylic-H), 4.48 (1H, d, J=11.1 Hz, benzylic-H), 4.53 (1H, d, J=11.9 Hz, benzylic-H), 4.57-4.64 (3H, benzylic-H, H-2), (1H, m,), 4.69 (1H, d, J=11.9 Hz, benzylic-H), 6.46 (1H, d, J=5.8 Hz, H-1), 7.02 (1H, m, imidazole-H), 7.22-7.40 (15H, m, aromatic-H), 7.73 (1H, m, imidazole-H), 9.40 (1H, bs, imidazole-H); $^{13}$C (100 MHz) δ$_C$(ppm): 36.0 (—N—CH$_3$), 68.0 (C-5), 72.5, 73.5 (benzylic-C), 78.2, 81.0, 82.6 (ring-C), 87.3 (C-1), 121.5, 122.5 (imidazole-C), 128.1-128.6 (aromatic-C), 135.5 (N—C=N), 136.4, 137.1, 137.2 (sat. aromatic-C); FABMS (m/z): 485.53.

Example 5

2,3,5-tri-O-benzyl-1-N-methylimidazolium-β-D-arabinofuranosyl tetra-fluoroborate In accordance with Xiao & Shreeve (J. Org. Chem., 70:3072-3078, 2005), 2,3,5-tri-O-benzyl-1-N-methylimidazolium-β-D-arabinofuranosyl chloride (1 mmol) was dissolved in a mixture of water and acetone (1:1, 10 mL) and treated with an aqueous solution of NaBF$_4$ (3 mmol). After 6 h, acetone was removed at reduced pressure. The water layer was extracted with EtOAc (3×15 mL). The combined organic layer was washed with water (3×15 mL), dried over MgSO$_4$, and evaporated in vacuo to give the compound that had incorporated the appropriate counter ion.

[α]$_D^{26}$=+9.5 (c1.05 CHCl$_3$); $^1$H NMR (400 MHz) CDCl$_3$ δ$_H$(ppm): 3.48 (3H, s, N—CH$_3$), 3.59 (1H, dd, J=3.2, 10.9 Hz), 3.76 (1H, dd, J=3.2, 10.9 Hz) (H-5, H-5'), 4.09 (1H, m, H-4), 4.18 (1H, t, J=6.4 Hz, H-3), 4.38 (1H, d, J=11.0 Hz, benzylic-H), 4.45 (1H, d, J=11.0 Hz, benzylic-H), 4.46-4.53 (4H, H-2, benzylic-H), 4.61 (1H, d, J=11.8 Hz, benzylic-H), 6.22 (1H, d, J=5.5 Hz), 7.16-7.36 (16H, aromatic-H, imidazole-H), 7.53 (1H, t, J=1.7 Hz,), 8.75 (1H, bs, imidazole-H); $^{13}$C (100 MHz) δ$_C$(ppm): 35.7 (—N—CH$_3$), 67.9 (C-5), 72.2, 73.1 (benzylic-C), 75.0, 78.3, 80.9, 82.1 (ring-C), 87.1 (C-1), 121.1, 122.1 (imidazole-C), 127.4-128.4 (aromatic-C), 134.9 (N—C=N), 136.3, 137.0, 137.1 (sat. aromatic-C); $^{19}$F (376.5 MHz) δ$_F$(ppm): −151.0.

Example 6

2,3,5-tri-O-benzyl-1-N-methylimidazolium-β-D-arabinofuranosyl hexa-fluorophosphate In accordance with Xiao & Shreeve (J. Org. Chem., 70:3072-3078, 2005), 2,3,5-tri-O-benzyl-1-N-methylimidazolium-β-D-arabinofuranosyl chloride (1 mmol) was dissolved in a mixture of water and acetone (1:1, 10 mL) and treated with an aqueous solution of NaPF$_6$ (3 mmol). After 6 h, acetone was removed at reduced pressure. The water layer was extracted with EtOAc (3×15 mL). The combined organic layer was washed with water (3×15 mL), dried over MgSO$_4$, and evaporated in vacuo to give the compound that had incorporated the appropriate counter ion.

[α]$_D^{26}$=+14 (c1.1 CHCl$_3$); T$_d$=175° C.; T$_g$=18° C.; $^1$H NMR (400 MHz) CDCl$_3$ δ$_H$(ppm): 3.41 (3H, s, N—CH$_3$), 3.58 (1H, dd, J=3.2, 10.9 Hz), 3.82 (1H, dd, J=3.3, 10.9 Hz) (H-5, H-5'), 4.09 (1H, m, H-4), 4.17 (1H, t, J=6.3 Hz, H-3), 4.37 (1H, d, J=11.0 Hz, benzylic-H), 4.57-4.64 (5H, benzylic-H, H-2), 4.61 (1H, d, J=11.9 Hz, benzylic-H), 6.05 (1H, d, J=5.5 Hz, H-1), 7.07 (1H, m, imidazole-H), 7.15-7.38 (15H, m, aromatic-H), 7.40 (1H, m, imidazole-H), 8.56 (1H, bs, imidazole-H); $^{13}$C (100 MHz) δ$_C$(ppm): 35.8 (—N—CH$_3$), 68.1 (C-6), 72.4, 73.3, 73.4 (benzylic-C), 78.5, 81.3, 82.3 (ring-C), 87.4 (C-1), 121.2, 122.7 (imidazole-C), 127.9-128.6 (aromatic-C), 134.8 (N—C=N), 136.4, 137.1, 137.2 (sat. aromatic-C); $^{19}$F (376.5 MHz) δ$_F$(ppm): −72.12, d, J=712 Hz; $^{31}$P (162 MHz) δ$_P$(ppm): −138.5, septet, J=712 Hz.

Example 7

2,3,5-tri-O-benzyl-1-N-methylimidazolium-β-L-arabinofuranosyl hexa-fluorophosphate Synthesis and characterization of the compound was as in Example 6. $^1$H NMR (400 MHz) CDCl$_3$ δ$_H$(ppm): 3.42 (3H, s, N—CH$_3$), 3.58 (1H, dd, J=3.3, 10.9 Hz), 3.75 (1H, dd, J=3.3, 10.9 Hz) (H-5, H-5'), 4.10 (1H, m, H-4), 4.17 (1H, t, J=6.2 Hz, H-3), 4.37 (1H, d, J=11.0 Hz, benzylic-H), 4.43-4.50 (5H, H-2, benzylic-H), 4.61 (1H, d, J=11.9 Hz, benzylic-H), 6.04 (1H, d, J=5.2 Hz), 7.05 (1H, t, J=1.7 Hz, imidazole-H), 7.14-7.36 (15H, aromatic-H), 7.38 (1H, t, J=1.7 Hz, imidazole-H), 8.56 (1H, bs, imidazole-H); $^{13}$C (100 MHz) δ$_C$(ppm): 35.9 (—N—CH$_3$), 68.3 (C-5), 72.6, 73.4, 73.5 (benzylic-C), 78.7 (C-3), 81.4 (C-4), 82.4 (C-2), 87.5 (C-1), 121.3, 122.8 (imidazole-C), 127.8-128.7 (aromatic-C), 134.9 (N—C=N), 136.5, 137.2, 137.3 (sat. aromatic-C).

Example 8

2,3,5-tri-O-benzyl-1-N-methylimidazolium-β-D-arabinofuranosyl bis(tri-fluoromethanesulfonyl) amide In accordance with Xiao & Shreeve (*J. Org. Chem.*, 70:3072-3078, 2005), 2,3,5-tri-O-benzyl-1-N-methylimidazolium-β-D-arabinofuranosyl chloride (1 mmol) was dissolved in a mixture of water and acetone (1:1, 10 mL) and treated with an aqueous solution of $LiN(SO_2CF_3)_2$ (3 mmol). After 6 h, acetone was removed at reduced pressure. The water layer was extracted with EtOAc (3×15 mL). The combined organic layer was washed with water (3×15 mL), dried over $MgSO_4$, and evaporated in vacuo to give the compound that had incorporated the appropriate counter ion.

Example 9

2,3,5-tri-O-benzyl-1-N-methylimidazolium-β-D-ribofuranosyl chloride $[\alpha]_D^{26}$=+21 (c1.55 $CHCl_3$); $T_d$=170° C.; $^1H$ NMR (400 MHz) $CDCl_3$ $\delta_H$(ppm): 3.47 (1H, dd, J=3.3, 10.7 Hz), 3.53 (1H, dd, J=3.4, 10.7 Hz) (H-5, H-5'), 3.82 (3H, s, N—$CH_3$), 4.01 (1H, dd, J=1.9, 5.2 Hz, H-3), 4.44 (1H, d, J=11.9 Hz), 4.51-4.55 (6H, benzylic-H), 4.59 (1H, bt, J=5.5 Hz, H-2,), 4.62 (1H, m, H-4), 6.23 (1H, d, J=5.8 Hz, H-1), 7.08 (1H, t, J=1.8 Hz, imidazole-H), 7.19-7.39 (15H, aromatic-H), 7.54 (1H, t, J=1.8 Hz, imidazole-H), 9.33 (1H, bs, imidazole-H); $^{13}C$ (100 MHz) $\delta_C$(ppm): 36.3 (—N—$CH_3$), 69.9 (C-5), 72.7, 73.6, 73.7 (benzylic-C), 77.2 (C-3), 78.4 (C-2), 84.9 (C-4), 88.2 (C-1), 121.8, 121.7, 127.8-128.6 (aromatic-C), 136.6 (N—C=N), 136.9, 137.0, 137.3 (sat. aromatic-C).

Example 10

2,3,5-tri-O-benzyl-1-N-methylimidazolium-β-D-xylofuranosyl chloride $^1H$ NMR (400 MHz) $CDCl_3$ $\delta_H$(ppm): 3.67-3.76 (2H, m, H-5, H-5'), 3.93 (3H, s, N—$CH_3$), 4.05 (1H, m, H-4), 4.22 (1H, t, J=5.3 Hz, H-3), 4.35-4.46 (3H, H-2, benzylic-H), 4.51 (1H, d, J=11.9 Hz, benzylic-H), 4.59 (1H, d, J=11.9 Hz, benzylic-H), 4.62-4.69 (2H, benzylic-H) 6.30 (1H, d, J=3.7 Hz), 7.08 (1H, bs, imidazole-H), 7.11-7.36 (15H, aromatic-H), 7.39 (1H, bs, imidazole-H), 9.26 (1H, bs, imidazole-H); $^{13}C$ (100 MHz) $\delta_C$(ppm): 36.3 (—N—$CH_3$), 68.7 (C-6), 72.5, 73.3 (benzylic-C), 75.0, 75.3, 78.0, 82.1 (ring-C), 85.0 (C-1), 121.1, 122.1, 127.7-128.5 (aromatic-C), 135.1 (N—C=N), 137.3, 137.7, 137.8, 137.9 (sat. aromatic-C).

Example 11

2,3,5-tri-O-benzyl-1-N-methylimidazolium-β-D-mannopyranosyl chloride $[\alpha]_D^{26}$=+10 (c1.15 $CHCl_3$); $^1H$ NMR (400 MHz) $CDCl_3$ $\delta_H$(ppm): 3.60-3.74 (6H, H-5, H-6, H-6', N—$CH_3$), 4.01 (2H, H—), 4.27 (1H, d, J=11.5 Hz, benzylic-H), 4.44 (1H, m, H—), 4.48-4.58 (3H, benzylic-H), 4.77 (1H, d, J=11.6 Hz, benzylic-H), 4.48-4.58 (3H, benzylic-H), 4.62 (1H, m, H-4), 5.89 (1H, s, H-1), 7.07-7.39 (16H, aromatic-H, imidazole-H), 7.56 (1H, bs, imidazole-H), 8.72 (1H, bs, imidazole-H); $^{13}C$ (100 MHz) $\delta_C$(ppm): 36.3 (—N—$CH_3$), 68.7 (C-6), 72.5, 73.3 75.0, 74.9 (benzylic-C), 73.3, 75.3, 78.0, 82.1 (ring-C), 85.0 (C-1), 121.1, 122.1, 127.7-128.5 (aromatic-C), 135.1 (N—C=N), 137.3, 137.7, 137.8, 137.9 (sat. aromatic-C).

Example 12

1-(2',3'-di-O-benzyl-β-D-arabinofuranosyl)-3-methylimidazolium chloride $^1H$ NMR (400 MHz) $CDCl_3$ $\delta_H$(ppm): 3.42 (3H, s, N—$CH_3$), 3.64 (1H, dd, J=2.1, 11.0 Hz), 3.82 (1H, dd, J=2.5, 11.0 Hz) (H-5, H-5'), 4.12 (1H, m, H-4), 4.21 (1H, t, J=3.8 Hz, H-3), 4.38 (1H, d, J=10.6 Hz, benzylic-H), 4.47 (1H, d, J=10.6 Hz, benzylic-H), 4.61 (1H, d, J=12.0 Hz, benzylic-H), 4.75 (1H, dd, J=5.8, 7.5 Hz, H-2), 4.86 (1H, d, J=12.0 Hz, benzylic-H), 6.02 (1H, d, J=5.8 Hz, H-1), 7.06 (1H, t, J=1.8 Hz, imidazole-H), 7.24-7.39 (15H, m, aromatic-H), 7.69 (1H, t, J=1.8 Hz, imidazole-H), 8.97 (1H, bs, imidazole-H); $^{13}C$ (100 MHz) $\delta_C$(ppm): 36.4 (—N—$CH_3$), 68.3 (C-5), 72.7, 74.1 (benzylic-C), 76.7, 77.9, 81.4 (ring-C), 89.6 (C-1), 122.0, 122.8 (imidazole-C), 128.4-129.1 (aromatic-C), 135.3 (N—C=N), 137.5, 138.1 (sat. aromatic-C).

Another compound that was synthesized is 2,3,5-tri-O-benzyl-1-N-methylimidazolium-β-D-galactofuranosyl chloride.

General Procedure for Debenzylation

The ionic liquid (1.55 mmol) was dissolved in ethanol (15 mL). To the resultant solution, $Pd(OH)_2$—C (100 mg) and cyclohexene were added. The mixture was heated at reflux for 7 days. The mixture was filtered through a pad of celite and concentrated in vacuo to provide crude product which was purified by silica gel chromatography eluted with $CHCl_3$:MeOH (8:2).

General Procedure for Addition of Diethylzinc

The solution of ionic liquid (0.5 mL), toluene (2 mL), and DCM (2 mL) was cooled to 0° C. Aldehyde (1 equivalent) and diethylzinc (3 equivalents) were added and stirred. After 30 min, a catalytic amount of TMSOTf was added, stirring continued for 5 h (reaction monitored by thin layer chromatography), and then dilution with 10 mL DCM. The reaction was quenched with 20 mL of sat. $NH_4Cl$. The mixture was extracted with EtOAc, combined organic layers dried over $MgSO_4$, and concentrated at room temperature. Residue was purified by successive column chromatography starting with $CHCl_3$:MeOH (9:1).

General Procedure for Grignard Reaction

To a stirred solution of ionic liquid (5 mmol) in 2 mL THF, methyl magnesium bromide in 3 M diethyl ether (0.55 mmol) was added under nitrogen at −78° C. After 30 min, aldehyde (0.5 mmol) was added and stirring continued for further 30 min. The reaction was quenched by adding 1 mL water and organic products were extracted with ether. They were purified either by successive silica gel column chromatography, initially with $CHCl_3$ then followed by chloroform:MeOH (8:2), or by preparative thin layer chromatography.

Patents, patent applications, books, and other publications cited herein are incorporated by reference in their entirety.

In stating a numerical range, it should be understood that all values within the range are also described (e.g., one to ten also includes every integer value between one and ten as well as all intermediate ranges such as two to ten, one to five, and three to eight). The term "about" may refer to the statistical uncertainty associated with a measurement or the variability in a numerical quantity which a person skilled in the art would understand does not affect operation of the invention or its patentability.

All modifications and substitutions that come within the meaning of the claims and the range of their legal equivalents are to be embraced within their scope. A claim which recites "comprising" allows the inclusion of other elements to be within the scope of the claim; the invention is also described by such claims reciting the transitional phrases "consisting essentially of" (i.e., allowing the inclusion of other elements to be within the scope of the claim if they do not materially affect operation of the invention) or "consisting of" (i.e., allowing only the elements listed in the claim other than impurities or inconsequential activities which are ordinarily associated with the invention) instead of the "comprising" term. Any of these three transitions can be used to claim the invention.

It should be understood that an element described in this specification should not be construed as a limitation of the claimed invention unless it is explicitly recited in the claims. Thus, the granted claims are the basis for determining the scope of legal protection instead of a limitation from the specification which is read into the claims. In contradistinction, the prior art is explicitly excluded from the invention to the extent of specific embodiments that would anticipate the claimed invention or destroy novelty.

Moreover, no particular relationship between or among limitations of a claim is intended unless such relationship is explicitly recited in the claim (e.g., the arrange-ment of components in a product claim or order of steps in a method claim is not a limitation of the claim unless explicitly stated to be so). All possible combinations and permutations of individual elements disclosed herein are considered to be aspects of the invention. Similarly, generalizations of the invention's description are considered to be part of the invention.

From the foregoing, it would be apparent to a person of skill in this art that the invention can be embodied in other specific forms without departing from its spirit or essential characteristics. The described embodiments should be considered only as illustrative, not restrictive, because the scope of the legal protection provided for the invention will be indicated by the appended claims rather than by this specification.

What is claimed is:

1. A chiral ionic liquid comprising a cation and an anion, wherein the cation is a sugar modified by replacing all but one hydroxyl group with protecting groups and replacing the one hydroxyl group with N-methylimidazolium linked directly to the sugar's anomeric carbon, which is liquid at atmospheric pressure and a temperature from 25° C. to 100° C.

2. The chiral ionic liquid of claim 1, wherein the sugar is a pentose or a hexose.

3. The chiral ionic liquid of claim 1, wherein the sugar is a furanose or a pyranose.

4. The chiral ionic liquid of claim 1, wherein the sugar is in the D form.

5. The chiral ionic liquid of claim 1, wherein the sugar is in the L form.

6. The chiral ionic liquid of claim 1, wherein the sugar is in the alpha configuration.

7. The chiral ionic liquid of claim 1, wherein the sugar is in the beta configuration.

8. The chiral ionic liquid of claim 1, wherein at least one protecting group is benzyl.

9. The chiral ionic liquid of claim 1, wherein the anion is selected from the group consisting of halides, acetates, aluminates, amides, borates, chlorates, cyanides, imidazoles, imides, iminos, iodates, nitrates, nitrites, phosphates, phosphonates, sulfates, and sulfonates.

10. A process of chemical separation, the process comprising:
    (a) at least partially or substantially solubilizing a mixture of chemicals in a mobile phase,
    (b) contacting the mobile phase with a stationary phase, and
    (c) separating at least one chemical from the mixture;
    wherein the mobile phase or the stationary phase or both are comprised of the chiral ionic liquid of claim 1.

11. A process of chemical separation, the process comprising:
    (a) at least partially or substantially solubilizing one or more chemical(s) in a solvent phase;
    (b) mixing the solvent mobile phase with an extraction phase, wherein the phases are immiscible; and
    (c) separating the chemical(s) by partition into the extraction phase;
    wherein the solvent phase or the extraction phase or both are comprised of the chiral ionic liquid of claim 1.

12. A process of chemical analysis, the process comprising:
    (a) at least partially or substantially solubilizing one or more chemical(s) in the chiral ionic liquid of claim 1 and
    (b) measuring an absorption or emission spectrum of the chemical(s).

13. An isolated chiral ionic compound consisting of a cation and an anion, which is liquid at atmospheric pressure and a temperature from 25° C. to 100° C., wherein the cation comprises a sugar modified by replacing all but one hydroxyl group with protecting groups and replacing the one hydroxyl group with N-methylimidazolium linked directly to the sugar's anomeric carbon.

14. A process of chemical separation, the process comprising:
    (a) at least partially or substantially solubilizing a mixture of chemicals in a mobile phase,
    (b) contacting the mobile phase with a stationary phase, and
    (c) separating at least one chemical from the mixture;
    wherein the mobile phase or the stationary phase or both are comprised of the chiral ionic compound of claim 13.

15. A process of chemical separation, the process comprising:
    (a) at least partially or substantially solubilizing one or more chemical(s) in a solvent phase;
    (b) mixing the solvent mobile phase with an extraction phase, wherein the phases are immiscible; and
    (c) separating the chemical(s) by partition into the extraction phase;
    wherein the solvent phase or the extraction phase or both are comprised of the chiral ionic compound of claim 13.

16. A process of chemical analysis, the process comprising:
    (a) at least partially or substantially solubilizing one or more chemical(s) in a solution comprised of the chiral ionic compound of claim 13 and
    (b) measuring an absorption or emission spectrum of the chemical(s).

* * * * *